(12) United States Patent
Saguet et al.

(10) Patent No.: US 11,166,969 B2
(45) Date of Patent: Nov. 9, 2021

(54) NUTRACEUTICAL AND/OR PHARMACEUTICAL COMPOSITION FOR STIMULATING THE PRODUCTION OF TYPE 2 BETA-DEFENSINS

(71) Applicant: USINES CHIMIQUES D'IVRY LA BATAILLE, Anet (FR)

(72) Inventors: Thibaut Saguet, Anet (FR); Laurent Lassalle, Anet (FR); Jean-Luc Philbe, Anet (FR); Florent Yvergnaux, Anet (FR)

(73) Assignee: USINES CHIMIQUES D'IVRY LA BATAILLE, Anet (FR)

( * ) Notice: Subject to any disclaimer, the term of this patent is extended or adjusted under 35 U.S.C. 154(b) by 57 days.

(21) Appl. No.: 16/607,249

(22) PCT Filed: Apr. 26, 2018

(86) PCT No.: PCT/FR2018/000101
§ 371 (c)(1),
(2) Date: Oct. 22, 2019

(87) PCT Pub. No.: WO2018/197762
PCT Pub. Date: Nov. 1, 2018

(65) Prior Publication Data
US 2020/0376010 A1    Dec. 3, 2020

(30) Foreign Application Priority Data

Apr. 26, 2017 (FR) ....................................... 1770423

(51) Int. Cl.
*A61K 31/702* (2006.01)
*A61P 1/00* (2006.01)

(52) U.S. Cl.
CPC .............. *A61K 31/702* (2013.01); *A61P 1/00* (2018.01)

(58) Field of Classification Search
None
See application file for complete search history.

(56) References Cited

FOREIGN PATENT DOCUMENTS

| FR | 2 996 138 A1 | 4/2014 |
|----|--------------|--------|
| WO | 2014/075745 A1 | 5/2014 |
| WO | 2014/092564 A1 | 6/2014 |

OTHER PUBLICATIONS

Lassalle, WO 2010106384 A1, Sep. 23, 2010, machine translation. (Year: 2010).*
Helliwell, Prof Nurse. Feb. 1993;8(5):313-7, abstract only. (Year: 1993).*
Boclé, Jean-Cristophe, "Effets des probiotiques et prébiotiques sur la flore et l'immunite de l'homme adulte," Agence Francaise De Securite Sanitaire, Feb. 2005, pp. 1-128.
Everard et al., "Microbiome of prebiotic-treated mice reveals novel targets invovled in host response during obesity," The ISME Journal, 2014, vol. 8, pp. 2116-2130.
Macfarlane et al., "Mucosal bacteria in ulcerative colitis," British Journal of Nutrition, 2005, vol. 93, Suppl. 1, pp. S67-S72.
Smith, Andrew P., "The concept of well-being: relevance to nutrition research," British Journal of Nutrition, 2005, vol. 93, Suppl. 1, S1-S5.
Cerezuela et al., "Increases in immune parameteres by inulin and Bacillus subtilis dietary administration to gilthead seabream (*Sparus aurata* L.) did not correlate with disease resistance to Photobacterium damselae," Fish & Shellfish Immunology, 2012, vol. 32, pp. 1032-1040.
Ivakhnenko et al., "Effect of the specific infant formula mixture of oligosaccharides on local immunity and development of allergic and infectious disease in young children: randomized study," Pediatria Polska, 2013, vol. 88, pp. 398-404.
Alizadeh et al., "The piglet as a model for studying dietary components in infant diets: effects of galacto-oligosaccharides on intestinal functions," British Journal of Nutrition, 2016, vol. 115, pp. 605-618.
Valdovska et al., "Alternative for improving gut microbiota: use of Jerusalem artichoke and probiotics in diet of weaned piglets", Polish Journal of Veterinary Sciences, 2014, vol. 17, No. 1, pp. 61-69.
Furrie et al., "Synbiotic therapy (Bifidobacterium longum/Synergy 1) initiates resolution of inflammation in patients with active ulcerative colitis: a randomised controlled pilot trial," Gut, 2005, vol. 54, pp. 242-249.
Djouzi et al., "Compared effects of three oligosaccharides on metabolism of intestinal microflora in rats inoculated with a human faecal flora," British Journal of Nutrition, 1997, vol. 78, pp. 313-324.
Sarbini et al., "In vitro fermentation of commercial α-glucooligosaccharide by faecal microbiota from lean and obese human subjects," British Journal of Nutrition, 2013, vol. 109, pp. 1980-1989.

(Continued)

Primary Examiner — Layla D Berry
(74) Attorney, Agent, or Firm — Oliff PLC

(57) ABSTRACT

A nutraceutical and/or pharmaceutical composition designed to stimulate the production of type 2 beta-defensins. The composition includes as a sole active ingredient a glucooligosaccharide presenting the following basic oligomeric structure:

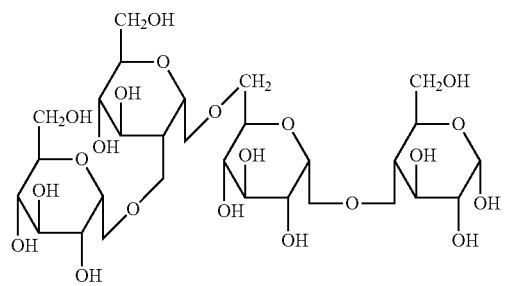

for the treatment of intestinal inflammations in the quantity of 0.5 to 10 g. Application to the treatment of functional colopathy.

10 Claims, No Drawings

(56) References Cited

OTHER PUBLICATIONS

Flickinger et al., "Glucose-Based Oligosaccharides Exhibit Different In Vitro Fermentation Patterns and Affect In Vivo Apparent Nutrient Digestibility and Microbial Populations in Dogs," Nutrient Metabolism, 2000, pp. 1267-1273.
"Full Public Report—Bioecolia (File No. NA/676)", National Industrial Chemicals Notification and Assessment Scheme, Jun. 1999, pp. 1-14.
Wehkamp et al., "NF-κB- and AP-1-Mediated Induction of Human Beta Defensin-2 in Intestinal Epithelial Cells by *Escherichia coli* Nissle 1917: a Novel Effect of a Probiotic Bacterium," Infection and Immunity, Oct. 2014, vol. 72, No. 10, pp. 5750-5758.
Jun. 13, 2018 International Search Report issued in International Patent Application No. PCT/FR2018/000101.

\* cited by examiner

NUTRACEUTICAL AND/OR PHARMACEUTICAL COMPOSITION FOR STIMULATING THE PRODUCTION OF TYPE 2 BETA-DEFENSINS

The technical field of the present invention is that of nutraceutical or pharmaceutical compositions designed to reduce inflammations of the digestive system and to limit the proliferation of certain microorganisms in the intestine.

The intestine is a complex and fragile environment in which numerous physiological processes take place. It is an environment in which numerous populations of microorganisms live and proliferate. Disruptions in these balances cause diseases and various disorders in the organism.

Numerous treatments are used for avoiding, treating, or attenuating such diseases, often with harmful effects on the commensal populations living in the intestine, thereby causing other negative symptoms that, in turn, need to be treated.

It has been known for a certain number of years that probiotics and prebiotics enhance good intestinal comfort and also make it possible to combat certain problems related to the intestine (AFSSA (*French Agency for Food, Environmental and Occupational Health and Safety*, Report by Boclé and Thomann, February 2005). Prebiotics are represented namely by fructo-oligosaccharides and by galacto-oligosaccharides.

For example, the interest of fructo-oligosaccharides to affect the intestinal flora, reduce obesity and type-2 diabetes has been shown (ISME Journal, 2014, 8, 2116).

By targeting and by increasing the intestinal quantity of certain families of bacteria, such as *Akkermansia muciniphila*, it is also possible to combat obesity even more effectively (Patent WO2014/075745). Intestinal inflammations can be reduced by the absorption of a mixture comprised of a probiotic of the *Bifidobacterium longum* type combined with a prebiotic of the fructo-oligosaccharide type (British Journal of Nutrition, 2005, 93S1, S67).

It has also been shown, in the sphere of immunity, that combining a prebiotic with a probiotic presents an action potential on immunity. For example, in a study conducted on sea breams, food supplemented with a prebiotic of the fructo-oligosaccharides type, and with a probiotic of the *Bacillus subtilis* type generates a significant reduction in the mortality of those fishes compared with the placebo group, which shows a link with improved immunity (Fish and Shellfish Immunology, 2012, 32, 1032). In addition, a study conducted on children receiving food supplementation with a prebiotic of the fructo-oligosaccharides and galacto-oligosaccharides types showed that those children exhibited improved immune defenses. However, during that study, a reduction in the salivary alpha-defensins was observed, contrary to what was observed in the control groups (Pediatria Polska, 2013, 88, 398).

Defensins are a family of peptide molecules that present antimicrobial properties in humans. There are alpha-defensins and beta-defensins whose role is, for example, to reinforce immunity or still to limit the proliferation of certain bacteria.

Among beta-defensins, there is the human type 2 beta-defensin, which is particularly important from a biological point of view and which is encoded by the DEFB4 (defensin, beta 4) gene. That beta-defensin exhibits a bactericidal potential against Gram-negative bacteria and against fungi of the *Candida* type. It is also part of the innate immune defense system. It contributes to maintaining a good balance in the human microbiome.

Prebiotics of the galacto-oligosaccharides or fructo-oligosaccharides types have recently shown potential for enhancing the production of such beta-defensins. Thus, it has been described in a study on piglets that using galacto-oligosaccharides in the food enhanced the production of beta-defensin-2 in the colons of the piglets (British Journal of Nutrition, 2016, 115, 605).

Another study shows that piglets whose feed supply is supplemented with a probiotic of the *Lactobacillus reuteri* and *Pediococcus pentosaceus* types and with Jerusalem artichoke, which is rich in fructo-oligosaccharide, exhibited an intestinal increase in the production of beta-defensins of the 2 and 3 types (Polish Journal of Veterinary Sciences, 2014, 17, 61).

A double-blind study with a supplementation in prebiotics of the *Bifidobacterium longum* type and fructo-oligosaccharides showed an increase in production of beta-defensin of types 2, 3, and 4 (Gut, 2005, 54, 242).

In the patent FR-2996138 is described the use of a gluco-oligosaccharide in the cutaneous production of antimicrobial peptides for dermo-cosmetic applications.

The literature examined above shows the benefits of prebiotics and probiotics for improving intestinal comfort. However, the use of oligosaccharides has not been fully explored and it has been observed that replacing one oligosaccharide by another does not necessarily provide the same effect.

Thus, the authors of a study conducted on rats showed different metabolic actions depending on the prebiotics ingested. It was concluded that the oligosaccharides studied (fructo-oligosaccharides, galacto-oligosaccharides and gluco-oligosaccharides) had different metabolic effects, to be related to their chemical structures (British Journal of Nutrition, 1997, 78, 313). More recently, a comparative study based on intestinal strains in contact with two sorts of prebiotics (gluco-oligosaccharides and fructo-oligosaccharides) showed significant metabolic differences (British Journal of Nutrition, 2013, 109, 1980). In 2000, this type of study was conducted on dogs and it was also shown that a modification in the chemical structure of the prebiotic administered led to different biological results (Am. Soc. For Nutr. Sci. 2000, 1267).

Thus, the aim of the invention is to provide an interesting treatment perfectly well tolerated by the organism that is intended to stimulate the production of the type 2 beta-defensin by the organism and, as a result, to cause a reduction or a disappearance of functional colopathy problems.

The invention thus relates to a nutraceutical and/or pharmaceutical composition intended to stimulate the production of type 2 beta-defensin, and characterized in that it comprises as sole active ingredient a gluco-oligosaccharide presenting the following basic oligomeric structure:

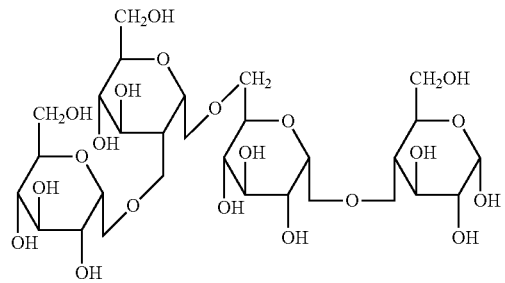

for the treatment of intestinal inflammations.

According to a characteristic of the invention, the composition comprises between 0.5 g and 10 g of gluco-oligosaccharide.

Advantageously, the composition comprises 1 g of gluco-oligosaccharide.

Even more advantageously, the composition comprises 2.5 g of gluco-oligosaccharide.

Even more advantageously, the composition comprises 4 g of gluco-oligosaccharide.

Even more advantageously, the composition comprises 6 g of gluco-oligosaccharide.

Even more advantageously, the composition comprises 9.5 g of gluco-oligosaccharide.

The invention further relates to the use of the composition to reduce or treat a functional colopathy.

The invention further relates to the use of the composition as a food supplement.

The composition according to the invention presents itself in the form of tablets or of capsules administered as a dose once per day.

An advantage of the pharmaceutical composition according to the invention is that it does not include any component that is aggressive for the intestinal microorganisms.

Another advantage lies in the fact that it does not destroy any of the microbial populations that are beneficial for the organism simultaneously with the elimination of the harmful populations.

Another advantage of the present invention lies in the absence of harmfulness of the composition even in the event of an overdose.

Another advantage of the present invention lies in the surprising activity of the gluco-oligosaccharide that is used alone as the active ingredient.

Another advantage of the present invention lies in a direct action at the intestinal mucus.

Other characteristics, advantages, and details of the invention will be better understood upon reading of the following supplementary description.

Intestinal infections are due, in part, to imbalances in the intestinal flora that promote pathogenic microorganisms, to the detriment of the commensal populations. Such imbalances have multiple causes, among which mention might be made of stress, fatigue, diet, and psychological state.

Prebiotics are oligosaccharides that enhance the development of microorganisms that are beneficial to the organism. Indeed, their structure makes them indigestible by the digestive system. Therefore, they are intact when they reach the colon, where they are a food source for the commensal microorganisms of the intestinal flora. Supplementing food with such prebiotics is known for improving digestive comfort and reducing infectious episodes.

The gluco-oligosaccharide of the invention is a prebiotic of this type that has already been used for its cosmetic properties on skin and for improving intestinal comfort. Intestinal comfort is understood as the "normal" state of functioning of the digestive system that is disrupted by the functional colopathy, commonly known as irritable bowel syndrome (IBS), which is an anomaly in the operation of the digestive tube.

Functional colopathy is a disorder of the operation of the colon. The colon is a portion of the intestine located between the small intestine and the rectum. It finishes off the digestion of food that starts in the small intestine, and it participates in the formation and evacuation of stools.

Due to a hypersensitivity of the colon, irritable bowel syndrome causes abdominal pain, constipation, diarrhea, and bloating. Although benign, this syndrome can manifest itself chronically and lead to a degradation in quality of life.

While studying the subject more thoroughly, the inventors discovered the surprising and unexpected effect of this gluco-oligosaccharide, when used alone, lying in its action of immune stimulation by promoting the production of beta-defensin-2.

Indeed, when the gluco-oligosaccharide is ingested, and apart from its use as food by the microorganisms present in the intestine, it comes in contact with the epithelial cells of the intestine. This contact induces an increasing of the production of type 2 beta-defensin in those cells of the organism.

The type 2 beta-defensin is a peptide of the defensins family. It is part of the immune system in which it plays two roles. Firstly, it reduces inflammation, and secondly it is capable of destroying certain germs, in this case, Gram-negative bacteria and fungi of the *Candida* type. The type 2 beta-defensin is one of the antimicrobial peptides (AMPS), which are microbicidal peptides.

The gluco-oligosaccharide according to the invention thus presents a therapeutic effect firstly on inflammations such as irritable bowel syndrome, and secondly on infections, by stimulating the production of type 2 beta-defensin.

A study was therefore conducted on a panel of 50 people presenting symptoms of irritable bowel syndrome.

The study was conducted in a monocentric manner with two groups in parallel (the group with the gluco-oligosaccharide and the placebo group), in a randomized, double-blind manner, and with a placebo control. The 50 subjects were adults presenting symptoms of irritable bowel syndrome associated with constipation. They were distributed randomly into two groups of 25 volunteers: one group treated with the gluco-oligosaccharide, and one group treated with a placebo (glucose). The safety and the effectiveness of the substance were assessed over a study with a length of treatment set at 28 days.

During a pre-inclusion visit, the subjects eligible for the study were investigated and selected on the basis of a questionnaire on the symptoms of irritable bowel syndrome and on dietary habits.

Stool samples were taken using a kit at the beginning of the study, on Day 0, and at the end of the study, on Day 28, for performing various assays, including, in particular that of type 2 beta-defensin. From Day 0 to Day 28, one group of volunteers took a daily dose of 2 g of gluco-oligosaccharide and the other group took a daily dose of 2 g of glucose as a placebo.

The treatment was very well tolerated by all of the subjects in the study and no negative effect was reported.

The findings obtained are described below:

The production of type 2 beta-defensin was characterized by the inventors by means of the ELISA (Enzyme-Linked Immunosorbent Assay) method.

Assessment of the quantity of type 2 beta-defensin (in nanograms (ng)/gram (g) of stool).

| Substances | Day 0 | Day 28 | Significance |
|---|---|---|---|
| Gluco-oligosaccharide | 51.28 | 62.33 | $p < 0.05$ |
| Placebo (glucose) | 49.77 | 54.52 | non-significant |

During the study, a significant increase in the production of intestinal type 2 beta-defensin was measured in the group treated with the gluco-oligosaccharide from the $1^{st}$ day of treatment to the $28^{th}$ day, while there was no significant increase for the group treated with the placebo. This increase for the group treated with the gluco-oligosaccharide is indicative of an increase in the defenses of the innate immunity of the intestinal mucus, with potential applications in a certain number of intestinal problems.

No side effect was observed. The use of the gluco-oligosaccharide thus opens up new avenue for the treatment of patients suffering from functional colopathy without any damage being done to the intestinal mucus.

The invention claimed is:

1. A method for stimulating production of type 2 beta-defensins to treat intestinal inflammation in a human, comprising administering to a human in need thereof a nutraceutical and/or pharmaceutical composition comprising, as sole active ingredient a gluco-oligosaccharide having the following oligomeric structure:

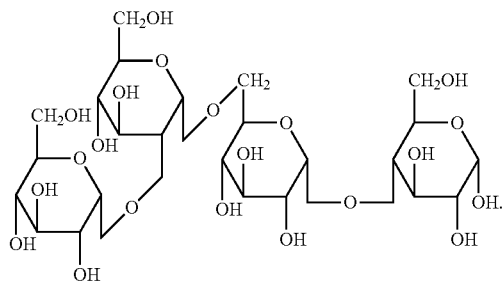

2. The method according to claim 1, wherein it comprises administering between 0.5 g and 10 g of gluco-oligosaccharide per day.

3. The method according to claim 2, wherein it comprises administering 1 g of gluco-oligosaccharide per day.

4. The method according to claim 2, wherein it comprises administering 2.5 g of gluco-oligosaccharide per day.

5. The method according to claim 2, wherein it comprises administering 4 g of gluco-oligosaccharide per day.

6. The method according to claim 2, wherein it comprises administering 6 g of gluco-oligosaccharide per day.

7. The method according to claim 2, wherein it comprises administering 9.5 g of gluco-oligosaccharide per day.

8. The method according to claim 1, wherein the nutraceutical and/or pharmaceutical composition is in the form of tablets or capsules administered as a dose once per day.

9. The method according to claim 1 wherein the method is for the reduction or the treatment of a functional colopathy.

10. The method according to claim 1 wherein the nutraceutical and/or pharmaceutical composition is a food supplement.

* * * * *